United States Patent [19]

Wood et al.

[11] Patent Number: 5,763,195

[45] Date of Patent: Jun. 9, 1998

[54] METHOD AND COMPOSITIONS FOR MAKING ACSF AND ACSF ANTAGONISTS

[75] Inventors: William I. Wood, San Mateo, Calif.; Thomas John Martin, Kew; Larry John Suva, East Kew, both of Australia

[73] Assignees: Genentech, Inc., South San Francisco, Calif.; University of Melbourne, Victoria, Australia

[21] Appl. No.: 425,491

[22] Filed: Apr. 20, 1995

Related U.S. Application Data

[62] Division of Ser. No. 330,137, Oct. 25, 1994, Pat. No. 5,656,455, which is a continuation of Ser. No. 785,158, Oct. 31, 1991, abandoned, which is a continuation of Ser. No. 216,678, Jul. 7, 1988, abandoned, which is a continuation of Ser. No. 52,637, May 20, 1987, abandoned.

[51] Int. Cl.$^6$ .................. G01N 33/53; G01N 33/573; C07K 16/30; A61K 39/395
[52] U.S. Cl. .................. 435/7.4; 435/7.23; 435/7.1; 435/7.92; 435/7.94; 435/7.93; 435/7.95; 435/7.71; 435/7.9; 424/130.1; 424/138.1; 424/158.1; 530/387.1; 530/387.7; 530/388.23
[58] Field of Search .................. 530/387.1, 387.7, 530/388.23; 435/7.94, 7.1, 7.4, 7.23, 7.92, 7.93, 7.71, 7.9; 424/130.1, 138.1, 158.1

[56] References Cited

U.S. PATENT DOCUMENTS

| 4,703,008 | 10/1987 | Lin | 435/240.2 |
|---|---|---|---|
| 4,968,669 | 11/1990 | Rosenblatt et al. | 435/240.2 |
| 5,114,843 | 5/1992 | Rosenblatt et al. | 435/7.2 |
| 5,116,952 | 5/1992 | Martin et al. | 530/399 |
| 5,149,779 | 9/1992 | Chorev et al. | 530/317 |

OTHER PUBLICATIONS

Cotram, R.S., et al., Robbins Pathological Basis of Disease, 4th ed., pp. 35–37, 292–296 (1989).
Abcloff, M.D., "Paraneoplastic Syndromes", New England J. Med., 317:1598–1600, (1987).
Broadus, A.E. et al., "Humoral Hypercalcemia of Cancer", New England J. Med., 319:556–563, (1988).
Suva et al., Gene, 77:95–105 (1989).
Vasicek et al., Proc. Natl. Acad. Sci., 80:2127–2131 (1983).
Hellerman et al., Proc. Natl. Acad. Sci., 81:5340–5344 (1984).
Lin et al., Proc. Natl. Acad. Sci., 82:7580–7584 (1985).
Suva et al., Science, 237:893–896 (1987).
Burtis et al., J. Biol. Chem., 262:15:7151–7156 (1987).
Stewart et al., Biochem. Biophys. Rsrch. Comm., 146:2:672–678 (1987).
Stewart et al., J. Bone and Mineral Rsrch., 1:3:267–276 (1986).
Stewart et al., J. Bone and Mineral Rsrch., 2:1:37–43 (1987).
Rosol et al., Cancer Rsrch., 47:3:690–695 (1987).
Seshadri et al., Clinical Science, 3:261–269 (1986).
Egan et al., Biochem. et Biophys. Acta, 483–496 (1980).
Wu et al., Clin. Endocrinology and Metabolism, 65:1:105–108 (1987).
Hendy, G.N., et al., "Gene for Parathyroid Hormone–Like Peptide is on Rat Chromosome 2", Biochem. Biophys. Rsrch. Comm., 157:2:558–562 (1988).
Mangin, Marguerite et al., "Identification of a cDNA encoding a parathyroid hormone–like peptide from a human tumor associated with humoral hypercalcemia of malignancy", Proc. Natl. Acad. Sci. USA, 85:597–601 (1988).
Mangin, Marguerite et al., "Isolation and Characterization of the human parathyroid hormone–like peptide gene", Proc. Natl. Acad. Sci. USA, 86:2408–2412 (1989).
Mosely, J.M., et al., "Parathyroid hormone–related protein purified from a human lung cancer cell line", Proc. Natl. Acad. Sci. USA, 84:5048–5052 (1987).
Nukada, Toshihide, et al., "Functional expression of cloned cDNA encoding the α–subunit of adenylate cyclase–stimulating G–protein", FEBS Letters, 211:1:5–9 (1987).
Schlesinger, David H., et al., "The Complete Amino Acid Sequence of Ubiquitin, an Adenylate Cyclase Stimulating Polypeptide Probably Universal in Living Cells", Biochem., 14:10:2214–2218 (1975).
Thiede, Mark A., et al., "Human renal carcinoma expresses two messages encoding a parathyroid hormone–like peptide: Evidence for the alternative splicing of a single–copy gene", Proc. Natl. Acad. Sci. USA, 85:4605–4609 (1988).
Thoriakay, Midory et al., "Synthesis of a Gene Encoding Parathyroid Hormone–Like Protein–(1–141): Purification and Biological Characterization of the Expressed Protein", Endo., 124:1:111–118 (1989).
Yasuda, Toshiyuki et al., "Characterization of the Human Parathroid Hormone–Like Peptide Gene", J. Biol. Chem., 264:13:7720–7725 (1989).
Merendino et al., "A parathyroid hormone–related protein from cultured human keratinocytes", Science, 231:388–390, (1986).
Rabbani et al., "Purification of peptides with parthyroid hormone–like bioactivity from human and rat malignancies associated with hypercalcemia", Endocrinology, 118:3:1200–1210, (1986).
Stewart et al., "Identification of adenylate . . . of malignancy", Proc. Natl. Acad. Sci., 80:1454–1458, (1983).
Scaver, S. S. (1994) Genetic Engineering News 14(14):10 & 21.

Primary Examiner—Lila Feisee
Assistant Examiner—John Lucas
Attorney, Agent, or Firm—Sughrue, Mion, Zinn, Macpeak & Seas, PLLC

[57] ABSTRACT

The complete amino acid and nucleotide sequence for adenylate cyclase stimulating factor is provided, thereby facilitating the synthesis of ACSF in recombinant cell culture. ACSF amino acid sequence variants and ACSF antibodies are provided which are useful in the treatment of humoral hypercalcemia of malignancy or in immunoassays for ACSF. In particular, antibodies capable of binding only the C–terminal domains of ACSF are useful in immunoassays for ACSF which avoid interference by parathyroid hormone. Also provided are novel polypeptides selected from the group of the ACSF basic peptide, the ACSF C–terminal peptide, or the ACSF domain containing both of the basic and C–terminal peptides.

12 Claims, 6 Drawing Sheets

```
brf.1         A  V  S  E  H  Q  L  L  H  D  K  G  K  S  I  Q  S  F  E  R  R  F  F  L
                              10            20            30            40            50            60            70
              GCTGTCTCTGAGCATCAGTGCTGCTGCATGACAAGGGCAAGTCCATCCAGTCCTTGAGCGGCGGTTCTTCCTG
              ***** ****** ********* ** ******* ** ******** ** ******** ** *********
brf.52        CGCCGCCTCAAAAGAGCTGTGTCTGAACATCAGCTCCTCCATGACAAGGGAAGTCCATCCAAGATTTACGGCGACGATTCTTCCTTCACCATCTGATCG
              420           430           440           450           460           470           480           490           500           510
              R  R  L  K  R  A  V  S  E  H  Q  L  L  H  D  K  G  K  S  I  Q  D  L  R  R  R  F  F  L  H  H  L  I brf.2         A  V  S  E  H  Q  L  L  H  D  K  G  K  S  I  Q  S  F  E  R  R  F  F  L
                              10            20            30            40            50            60            70
              GCTGTGAGTGAACATCAGTGTCTGTCTGAACATCAGCTCAGCATCAGCTCCTCCATGACAAGGGCAAGTCCAAATCCATCCAGTCCTTGAGAGACGGTTCTTCCTG
              ****** ** *********** ** **  *** ** ******** ** ******** *  ********
brf.52        CGCCGCCTCAAAAGAGCTGTGTCTGAACATCAGCTCCTCCATGACAAGGGAAGTCCATCCAAGATTTACGGCGACGATTCTTCCTTCACCATCTGATCG
              420           430           440           450           460           470           480           490           500           510
              R  R  L  K  R  A  V  S  E  H  Q  L  L  H  D  K  G  K  S  I  Q  D  L  R  R  R  F  F  L  H  H  L  I
```

FIG. 1

```
                                                                                           hgaI
 -22  GTCCCGAGCC CGAGCGGAGA CGATGCAGCG GAGACTGGTT CAGCAGTGGA GCGTCGGCGT GTTCCTGCTG AGCTACGCGG TGCCCTCCTG CGGGCGCTCG
 -36                         M  Q  R   R  L  V   Q  Q  W  S   V  A  V   F  L  L   S  Y  A  V   P  S  C   G  R  S 79  GTGGAGGGTC TCAGCGCCCG TCTCAAAGA GCTGTGTCTG ACATCAGCT CCTCCATGAC AAGGGAAGT CCATCCAAGA TTTACGGCGA CGATTCTTCC
 -10   V  E  G  L  S  R  R   L  K  R    A  V  S  E   H  Q  L  L  H  D   K  G  K  S   I  Q  D   L  R  R   R  F  F  L
                                    pvuII                        10                                    20

179  TTCACCATCT GATCGCAGAA ATCCACACAG CTGAAATCAG AGCTACCTCG GAGGTGTCCC CTAACTCCAA GCCCTCTCCC AACACAAAGA ACCACCCCGT
  25   H  H  L  I   A  E    I  H  T  A   E  I  R    A  T  S   E  V  S  P   N  S  K   P  S  P   N  T  K  N   H  P  V
                                                 40                               50

279  CCGATTGGG TCTGATGATG AGGGCAGATA CCTAACTCAG GAACTAACA AGTGGAGAC GTACAAAGAG CAGCCGCTCA AGACACCTGG GAAGAAAAG
  58   R  F  G  S  D  D  E   G  R  Y   L  T  Q    E  T  N  K   V  E  T    Y  K  E   Q  P  L  K   T  P  G   K  K  K
                         smaI                 70                                80                                 90

379  AAGGCAAGC CCGGGAAACG CAAGGACCAG GAAAAGAAAA AACGGCGAAC TGCTCTGCC TGGTTAGACT CTGGAGTGAC TGGAGTGGG CTAGAAGGG
  91   K  G  K  P  G  K  R   K  E  Q    E  K  K  K   R  R  T   R  S  A   W  L  D  S   G  V  T   G  S  G   L  E  G  D
                              100                     sacI                     110                             120

479  ACCACCTGTC TGACACCTCC ACAACGTCGC TGGAGCTCGA TTCACGGAGG CATTGAAATT TTCAGCAGAG ACCTTCCAAG GACATATTGC AGGATTCTGT
 125   H  L  S   D  T  S    T  T  S  L   E  L  D    S  R  R   H  Q
                 130                                         140
                                                                                                        draI
 579  AATAGTGAAC ATATGGAAAG TATTAGAAAT TTTTTTTTTG GTAAATACT CCAATTATT ATTACACAT CTTGCTCTA TGAACTGCA ATTTTAAATT
 679  CATTGGTCAT TGTGAATATT TGTGAATATT CCAAGGCTAA TCCAATTATT TTACCATAAT ACATATCAAG TTATTTGT CATTGATGTA TTTATTTGT
 779  AAATGTATCT TGGTGCTGCT GAATTTCTAT ACATACTGTA CTTAGATAT ACATATCAAG TATGTTGATA AATGACACAA TGAAGTGTCT
 879  CTATTTGTG GTTGATTTA ATGAATGCCT AAATATAATA ATCCAAATTG ATTTCCTTC GTGCATGTAA AAATAACAGT ATTTAAATT TGTAAAGAAT
 979  GTCTAATAAA ATATAATCTA ATTAC
```

```
           GGCTGCTGCA TGTCAAGGGC AAGAGGAACG TGGTAGCTGG AGAGGTAGAG ATGTCCTGGA AGAGTTTCA
           CCGACGACGT ACAGTTCCCG TTCTCCTTGC ACCATCGACC TCTCCATCTC TACAGGACCT TCTCAAAGT
      A57  LeuLeuHi sValLysGly LysArgAsnV alValAlaGl yGluValGlu MetSerTrpL ysSerPheTh r
      ACSF: LeuLeuHi sAspLysGly LysSer

CGAGGGGATG TTTTCCTCCT GGACCTTGGG AAGCTTATCA TCCAGTGGAA TGGACCCGGAA AGCACCCGTA
           GCTCCCCTAC AAAAGGAGGA CCTGGAACCC TTCGAATAGT AGGTCACCTT ACCTGGCCTT TCGTGGGCAT
           ArgGlyAspV alPheLeuLe uAspLeuGly LysLeuIleI leGlnTrpAs nGlyProGlu SerThrArgM

TGGAGAGACT CAGGGGCATG ACTCTGGCCA AGGAGATCCG AGACCAGGAG CGGGGAGGGC
           ACCTCTCTGA GTCCCCGTAC TGAGACCGGT TCCTCTAGGC TCTGGTCCTC GCCCCTCCCG
           etGluArgLe uArgGlyMet ThrLeuAlaL ysGluIleAr gAspGlnGlu ArgGlyGlyArg

GCACCTATGT AGGCGTGGTG GACGGAAGAG AATGA
           CGTGGATACA TCCGCACCAC CTGCCTTCTC TTACT
           ThrTyrVa lGlyValVal AspGlyArgG luDP*
```

FIG. 6

METHOD AND COMPOSITIONS FOR MAKING ACSF AND ACSF ANTAGONISTS

This is a divisional of application Ser. No. 08/330,131 filed 25 Oct. 1994, now U.S. Pat. No. 5,656,499 which is a continuation of application Ser. No. 785,158 filed 31 Oct. 1991, now abandoned which is a continuation of U.S. Ser. No. 216,678 filed 7 Jul. 1988, now abandoned which is a continuation of U.S. Ser. No. 07/052,637, filed 20 May 1987 now abandoned.

BACKGROUND OF THE INVENTION

This invention relates to the polypeptide ACSF (adenylate cyclase stimulating factor) and substances which antagonize the activity of ACSF in vivo. In particular, this invention relates to DNA encoding ACSF and methods for the use of such DNA to produce ACSF and its polypeptide antagonists, including amino acid sequence variants and antibodies directed against selected ACSF epitopes. This invention also relates to therapeutic compositions containing ACSF antagonists particularly for the treatment of hypercalcemia attendant upon various neoplasms.

A variety of cancers are clinically associated with non-metastatic bone destruction and serum hypercalcemia (humoral hypercalcemia of malignancy, or HHM), most commonly breast, lung and skin carcinomas, but the phenomenon is by no means limited to these cancers. Soluble factor(s) released by the tumor cells which have been thought in the past to be responsible for HHM, include transforming growth factors, parathyroid hormone, prostaglandins, and other relatively uncharacterized factors. For an extensive review on this subject, see Mundy et al., "New England Journal of Medicine" 310:1718 (1984). More recently, reports have appeared of substances partially purified from murine tumors, rat Leydig cell and human HHM tumors which stimulate the parathyroid hormone (PTH) receptor, exert adenylate cyclase activity, and are inhibited by the PTH antagonist $Nle^{8,18}, Tyr^{34}$bovine PTH (3-34) amide and which have a molecular weight in the range of 30–40 kD (Rodan et al., "J. Clin. Invest." 72:1511 [1983]; Strewler et al., "J.Clin. Invest.", 71:769 [1983]; Stewart et al. "Clin. Res." 32:410A [1984]; Merendino et al., "Science" 231:388 [1986]; Insogna et al. "Endocrinology" 120:2183 [1987]; Stewart et al., "J. Bone and Mineral Research" 1:267 [1986]; and Burtis et al., "Endocrinology" 118:1982 [1986]). No amino acid sequence data for these factor(s) was disclosed by these authors, nor had the plurality of candidate factors been explained at a molecular level.

In work which, as of the filing date hereof, remains unpublished, Dr. T. J. Martin and colleagues have purified to homogeneity an ACSF from an HHM squamous carcinoma (BEN) cell extract and determined the amino terminal amino acid sequence of the factor:

```
  1           11      * * *    21
  A V S E H Q L L H D K G K S I Q X F E R R F F L
```

Uncertain residues are designated by asterisks.

Peptide analogues based on the first 17 residues from this sequence were synthesized: Ala-Val-Ser-Glu-His-Gln-Leu-Glu-His-Asn-Cys ($[Glu^8, Asn^{10}, Cys^{11}]$ ACSF [1-11], Ala-Val-Ser-Glu-His-Gln-Leu-Leu-His-Asn-Lys-Gly-Lys-Ser-Ile-Gln ($[Asn^{10}]$ ACSF [1-16]) and $[Asn^{10}, Tyr^{17}]$ ACSF (1-17). The analogs, $[Glu^8, Asn^{10}, Cys^{11}]$ ACSF (1-11) and $[Asn^{10}]$ ACSF (1-16) were inactive in the adenylate cyclase assay and did not antagonize the action of PTH itself or of conditioned medium from BEN cells. $[Glu^8, Asn^{10}, Cys^{11}]$ ACSF (1-11) conjugated to soya bean trypsin inhibitor was used to immunize rabbits against ACSF, and an antiserum produced which was used in radioimmunoassay.

In order to treat patients afflicted with HHM it is necessary to provide an ACSF antagonist. It is a first objective herein to obtain DNA encoding ACSF in order to obtain the complete amino acid sequence thereof. This will facilitate the preparation of ACSF and ACSF antagonists in recombinant cell culture. In addition, C-terminal sequence for ACSF will allow one to prepare antibodies specific for this domain of ACSF, thereby improving immunoassays for ACSF. These and other objects of the invention will be apparent from consideration of the specification in its entirety.

SUMMARY OF THE INVENTION

The objects of this invention are accomplished by is providing nucleic acid encoding ACSF, transforming a host cell with the nucleic acid, and culturing the host cell whereby ACSF is expressed in the culture. Preferably the ACSF is recovered from the cell culture.

Nucleic acid is provided that hybridizes to DNA encoding ACSF under conditions of low stringency. This nucleic acid, which may or may not encode ACSF, is used to probe to identify nucleic acid encoding ACSF in cDNA libraries, mRNA preparations or genomic DNA libraries.

Nucleic acid that in fact encodes ACSF is used as a probe for the same purposes as is hybridizing nucleic acid. It serves the additional function of enabling the expression of ACSF upon insertion into an expression vector such as a virus or plasmid, followed by transfection into host cells such as bacteria, yeast or mammalian cells and culturing the transformants for expression of ACSF.

Included within the scope of this invention are ACSF antagonists. Such antagonists include antibodies (polyclonal or monoclonal) which are capable of neutralizing the biological activity of ACSF, antagonist amino acid sequence variants, or ACSF immunogens which are capable of raising neutralizing antibodies in vivo in patients.

Therapeutic ACSF antagonist compositions are provided that are useful in the treatment of HHM. These compositions optionally include supplemental therapeutics such as TGF-α antagonists, EGF antagonists, and PTH antagonists.

The ACSF C-terminus is described herein. This region contains an amino acid sequence having no sequence homology whatsoever with PTH. The ACSF C-terminal region is useful in the preparation of antibodies which do not cross-react with PTH and which therefor would be particularly useful in immunoassays for ACSF, in particular in sandwich-type immunoassays employing antibody against the N-terminal epitope as well as the C-terminal epitope. Antibodies against the C-terminal region also will be of therapeutic use in the treatment of HHM or conditions having similar sequelae.

BRIEF DESCRIPTION OF THE DRAWINGS

FIG. 1 depicts the nucleotide sequences of the two 72mer probes (brf. 1 and brf. 2) constructed in accordance with the amino acid sequence of ACSF (upper lines) compared to the corresponding sequence of the ACSF cDNA (lower lines). Homologous nucleotides are highlighted with asterisks.

FIG. 2 is the nucleotide and amino acid sequence of ACSF clone brf.52. Several restriction enzyme cleavage sites are indicated.

FIG. 3 is a comparison of the amino acid sequences for human ACSF with those of PTH for three animal species and with human PTH. Completely homologous residues are boxed.

FIG. 6 is the partial nucleotide and amino acid sequence of a polypeptide identified in BEN cell cDNA which contains a region homologous with ACSF.

DETAILED DESCRIPTION OF THE INVENTION

Figure 4:
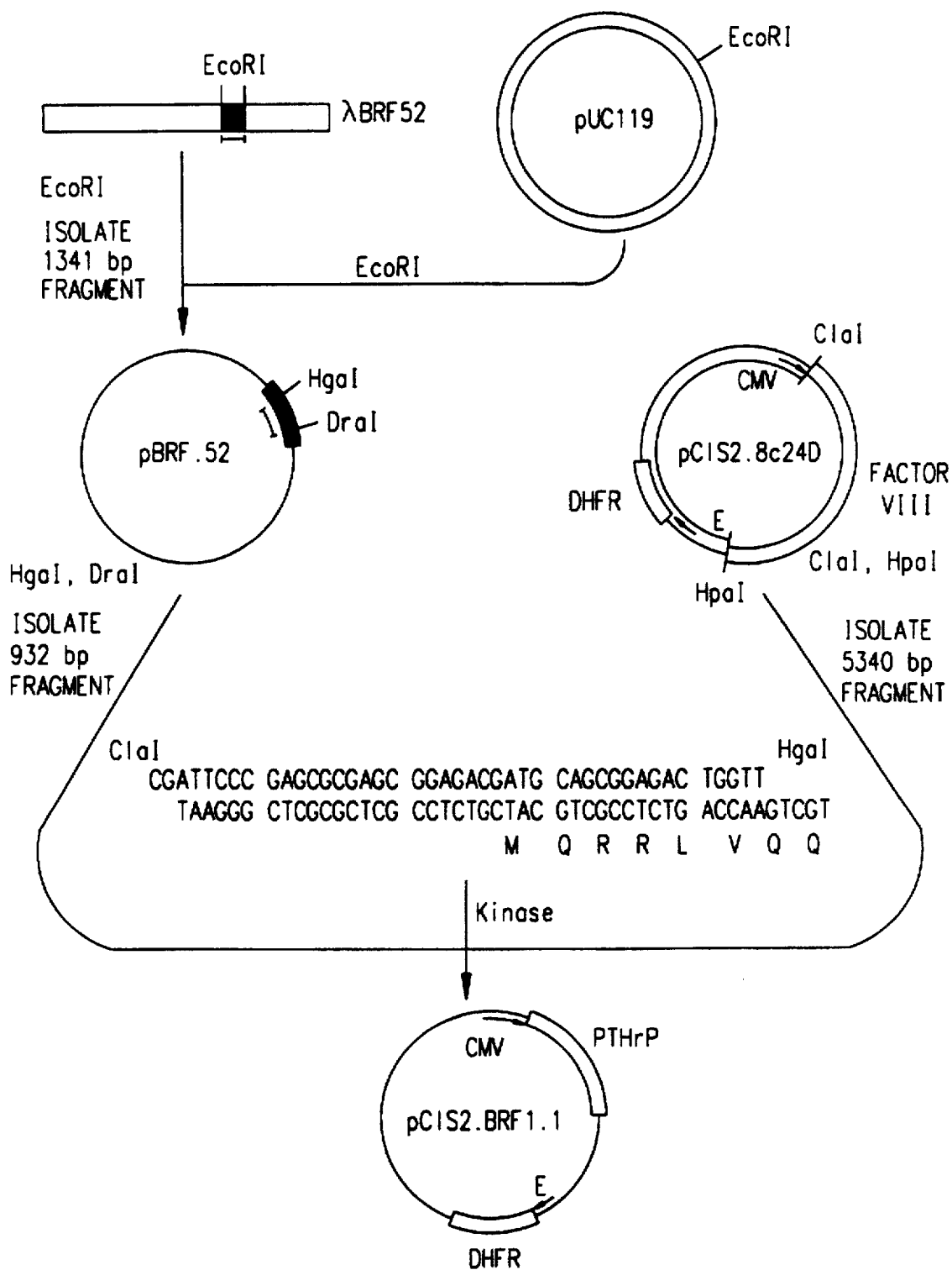
FIG. 4 depicts a suitable method for the construction of an expression vector for an ACSF. Briefly, the ACSF gene is recovered from the λ clone brf.52 and spliced into a cloning vector pUC119. The cloned gene is recovered and ligated with an oligonucleotide encoding the N-terminus into the expression vector pCIS2.8c24D in order to construct expression vector pCIS2.BRF1.1.

For the purposes of this invention, ACSF is defined as the class of proteins or polypeptides which are biologically active and which have the amino acid sequence set forth in FIG. 2, as well as proteins or polypeptides which represent substitutional, deletional or insertional variants of the FIG. 2 sequence, excluding PTH or its known agonist or antagonist analogues.

Structurally, the FIG. 2 sequence represents preACSF consisting of a 31 residue signal followed by a 5 residue basic pro sequence and the sequence of mature ACSF. Mature ACSF contains three principal domains. The most N-terminal of these, extending about from residue 1 to residue 83 and termed the N-terminal domain, contains sequence which is in part homologous to PTH and may therefore contain the PTH receptor binding functionality of ACSF. Thereafter in the C-terminal direction lies a highly basic region extending about from residues 84 to 108, termed the basic peptide, and finally the C-terminal peptide at about residues 109 to 141. The C-terminal peptide may be responsible for one or more of the effects of HHM not attributable to PTH activity, e.g., decreases in plasma 1,25-dihydroxyvitamin D, gut adsorption of calcium, and renal tubular calcium readsorption, as well as the impairment of bone formation.

Biologically active means that the ACSF protein or polypeptide qualitatively exerts at least one known or inherent activity of ACSF having the FIG. 2 amino acid sequence or, if not having such activity, (a) acting antagonistically towards that activity or (b) capable of cross-reacting with an antibody raised against ACSF having the FIG. 2 sequence.

Known ACSF biological activities, aside from the ability to raise anti-ACSF antibodies, include one or more of adenylate cyclase stimulating activity, PTH receptor binding activity, and bone resorbing activity. Preferably, ACSF is assayed in a biological system making use of the dose-dependent generation of cyclic AMP in osteoblast-like cells while antagonists are most directly assayed in BEN cell-bearing nude mice demonstrating hypercalcemia or in the rat Leydig cell model. There are several ways in which the assay can be carried out, including direct measurement of adenylate cyclase activity in membrane homogenates of osteoblast-like cells, and assay of cyclic AMP generated by intact cells. For simplicity, convenience and to allow ready assay of very large numbers of samples, responses are assayed by making several dilutions of test sample in culture medium, growing UMR 106-01 (Martin et al., "Nature" 260:436 [1976]) cells as replicate cultures in 12-well plastic dish containing control and test media, labelling the cellular ATP pool with $^3$H by preincubating for 2 hours with $^3$H-adenine, washing the cells briefly, then adding 1 mM isobutylmethylxanthine, a phosphodiesterase inhibitor. After 10 minutes reactions are stopped and $^3$H-cyclic AMP purified from incubates by sequential chromatography on DOWEX (Registered trade mark (ion exchange resin)) and neutral alumina. The cells respond to PTH and to prostaglandins of the E series (principally $PGE_2$) with dose-dependent increases in cyclic AMP formation. The response to PTH in this assay, but not that to $PGE_2$, is inhibited by prior incubation of samples with peptide antagonists of PTH (Kubota et al., "J. Endocrinology" 108:261 [1986]) or other antiserum to PTH prepared against synthetic human PTH (1-34).

Substitutional, deletional or insertional variants of the FIG. 2 sequence will have one or more of the following activities: ACSF antagonist, ACSF agonist, or anti-ACSF cross-reactivity. While animal analogues (for example bovine or porcine ACSF) of the human ACSF sequence shown in FIG. 2, and allelic variants of such ACSF species variants, will have ACSF activity, it generally will be necessary to screen each construction in the in vitro or in vivo bioassays described above, or to use the construction in an immunoassay protocol in order to determine its ACSF cross-reactivity, in accordance with procedures known per se.

ACSF antagonist and agonist activity preferably is measured in the UMR cell bioassay in the same fashion as ACSF except that serial dilutions of the candidate are made in culture medium containing ACSF having the FIG. 2 mature sequence. Antagonists are identified by their ability to suppress ACSF-mediated cAMP generation in the test cells; agonists are identified by their stimulatory effect.

ACSF variants which are immunologically cross-reactive with antisera raised in rabbits by immunization against FIG. 2 ACSF also may serve as ACSF immunogens. ACSF immunogens are identified by their ability to raise antisera in rabbits which cross-reacts with FIG. 2 ACSF. A typical immunization protocol is employed in which rabbits are inoculated subcutaneously with a preparation of the candidate in Freunds complete adjuvant, followed by sequential boosters in Freunds incomplete adjuvant by the same route of administration. It may be necessary to formulate the ACSF with alum or cross-link it with glutaraldehyde in order to raise a response having detectable titer. The animals are assayed for anti-ACSF at the end of the first month after the first inoculation and at the end of each of the following two months.

In general, ACSF amino acid sequence variants are characterized by substitutions, deletions or insertions of amino acid residues within the following mature ACSF sequences, referring to the residue numbers set forth in FIG. 2: 1–34 inclusive, 50, 53, 79, and 81–141 inclusive.

Insertions are introduced adjacent to the indicated residues at either the N or C-terminal peptidyl bonds, and preferably are introduced in pairs. Insertions typically will range from 1 to about 30 residues, with 2 being the preferred insertion. However, when it is desired to insert an immunogenic sequence the insertion may be of any size suitable for this purpose, often in excess of 100 residues. ACSF immunogens ordinarily are insertional variants wherein the immunogenic sequence is introduced at the N or C terminus of ACSF or a fragment thereof which bears the target epitope. For example, DNA encoding an immunogenic fragment of the E. coli trpD, trpE or Staphylococcal Protein A genes is ligated at its 5' or 3' terminus to the 5' or 3' terminus of DNA encoding ACSF and expressed in recombinant cell culture in order to prepare an ACSF immunogen. For example, the region containing the basic peptide and the C-terminal peptide is linked at an N-terminal residue to the C-terminal residue of an immunogenic polypeptide (generally, a bacterial polypeptide) in order to prepare an immunogen capable of raising antibodies against the C-terminal domains of ACSF. Similarly, insertion of a signal sequence N-terminal to a residue extending about from 84 to 107 of ACSF (together with deletion of ACSF residues from 1–83 to 106 as the case may be) will be useful in secreting ACSF C-terminal domains from recombinant cell culture. Expression of DNA encoding mature ACSF in the cytoplasm, i.e., without a signal sequence, will produce an insertional variant wherein the mature sequence contains an additional N-terminal methionyl residue resulting from translation of the start codon inserted in place of the FIG. 2 signal sequence. This variant is termed methionyl mature ACSF. Other representative insertional variants include mature ACSF linked at its N-terminus to the bacterial signal sequences for alkaline phosphatase or STII enterotoxin, or to a yeast alpha factor signal, $[V_2GGS_3]ACSF(1-141)$; $[V_2SS_3]ACSF(1-141)$; $[V_2EKA_3]ACSF(1-141)$; $[G_{123}PPD_{124}]ACSF(3-141)$; $[S_{130}FYT_{131}]ACSF(3-141)$; $[R_{139}DYR_{140}]ACSF(3-141)$; $[V_2AGS_3]ACSF(1-141)$; $[T_{132}KKKS_{133}]ACSF(1-141)$; $[S_3EEE_4]ACSF(1-34)$; $[E_4IH_5]ACSF(1-34)$; $[E_4IH_5DQ_6]ACSF(1-34)$; and $[P_{44}DN_{45}]ACSF(1-141)$. Such variants, to the extent they do not exhibit ACSF agonist or antagonist activity, will cross-react with antibody to ACSF and therefore be useful as ACSF immunogens or for use in ACSF immunoassays as standards or controls. It will be apparent that many variants will contain combinations of substitutions, deletions and insertions.

Deletional variants of ACSF also can be made by the recombinant method herein. Deletional variants ACSF(1-83) and ACSF(1-34) have PTH activity. Other deletional variants include ACSF(1-84, 109-141), ACSF(1-34, 40-141), ACSF(1-50, 60-141), ACSF(1-75, 84-141), ACSF (1-109) (ACSF(3-34), ACSF(4-34), ACSF(5-34), ACSF(6-34) and ACSF(3-124). Preferred deletions are of or within about residues 1–35 and 85–141; generally ACSF residues after 34 will be present in deletional variants. Such variants contain ACSF epitopes, so to the extent they are not agonists or antagonists for ACSF, they will cross-react with antibody to ACSF. Also included are deletions from ACSF wherein comparable sequences from PTH are inserted in their place, e.g. PTH(7-34) ACSF(35-141) or PTH(3-34)ACSF(35-141).

Most commonly, ACSF variants will be substitutional variants, those in which at least one residue in ACSF has been deleted and another residue inserted in its place. Substitutions typically are made in accord with the following table:

TABLE 1

| Original Residue | Exemplary Substitutions |
| --- | --- |
| Ala | gly; ser |
| Arg | lys |
| Asn | Gln; his |
| Asp | glu |
| Cys | ser |
| Gln | asn |
| Glu | asp |
| Gly | ala |
| His | asn gln |
| Ile | leu; val |
| Leu | ile; val |
| Lys | arg; gln; glu |

TABLE 1-continued

| Original Residue | Exemplary Substitutions |
| --- | --- |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions in general expected to produce the greatest changes in ACSF properties will be those in which (a) a hydrophilic residue, e.g. seryl or threonyl, is substituted for (or by) a hydrophobic residue, e.g. leucyl, isoleucyl, phenylalanyl, valyl or alanyl; (b) a proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having such a side chain, e.g., glycine.

Representative substitutional variants are introduced at one of residues 1–9, 12–15, 20, 23–28, 31–32, 49–50, 53, 59–61, 79–82, 86–98, 104–105, 115, 118, 120, 123, 127–133 and 139–140, preferably 1–9 and 109–141. Examples include $[MY_1]ACSF(1-141)$, $[MP_1]ACSF(1-141)$, $[MG_1]ACSF(1-141)$, $[F_2]ACSF(1-141)$, $[Y_2]ACSF(1-141)$, $[H_2]ACSF(1-141)$, $[D_3]ACSF(1-141)$, $[Y_3]ACSF(1-141)$, $[H_3]ACSF(1-141)$, $[K_{20}]ACSF(1-141)$, $[E_{19}]ACSF(1-141)$, $[V_{21}]ACSF(1-141)$, $[D_{20}]ACSF(1-141)$, $[Y_{24}]ACSF(1-141)$, $[K_{25}]ACSF(1-141)$, $[E_{25}]ACSF(1-141)$, $[M_{31}]ACSF(1-141)$, $[Y_{34}]ACSF(3-141)$, $[I_8, I_{18}, Y_{34}]ACSF(3-141)$, $[I_8, I_{18}, Y_{34}]ACSF(3-34)$, $[D_{79}]ACSF(1-141)$, $[P_{98}]ACSF(1-141)$, $[P_{105}]ACSF(1-141)$, $[Y_{90}]ACSF(1-141)$, $[W_{89}]ACSF(1-141)$, $[H_{96}]ACSF(1-141)$, $[F_{110}]ACSF(106-141)$, $[Y_{117}]ACSF(106-141)$, $[D_{122}]ACSF(106-141)$, $[K_{125}]ACSF(106-141)$, $[Y_{132}]ACSF(106-141)$, $[A_{133}]ACSF(106-141)$, and $[D_{141}]ACSF(106-141)$. These variants contain ACSF epitopes and accordingly will be useful as immunoassay reagents or immunogens notwithstanding agonist or antagonist activities that they may possess.

Most deletions and insertions, and substitutions in particular, will not produce radical changes in the characteristics of the ACSF molecule. However, when it is difficult to predict the exact effect of the substitution, deletion or insertion in advance of doing so, for example when modifying the PTH receptor binding domain or an immune epitope, one skilled in the art will appreciate that the effect will be evaluated by routine screening assays. For example, a variant typically is made by site specific mutagenesis of the native ACSF encoding nucleic acid, expression of the variant nucleic acid in recombinant cell culture and, optionally, purification from the cell culture for example by immunoaffinity adsorption on a rabbit polyclonal anti-ACSF column (in order to adsorb the variant by at least one remaining immune epitope). Alternately, low molecular weight variants, e.g. those having less than about 50 residues, are conveniently produced by in vitro synthetic methods. This provides an opportunity to introduce non-natural amino acids, e.g. D-amino acids, into ACSF sequences. The activity of the synthetic variant, cell lysate or purified ACSF variant is then screened in a suitable screening assay for the desired characteristic. For example, a change in the immunological character of ACSF, such as affinity for a given antibody, is measured by a competitive-type immunoassay. Changes in adenylate cyclase stimulating activity are measured by a bioassay, although as more becomes known about ACSF functions in vivo other assays will become useful in such screening. Modifications of such other ACSF properties as redox or thermal stability, pI, hydrophobicity, susceptibility to proteolytic degradation, or the tendency to aggregate with carriers or into multimers are assayed by methods well known to the artisan.

Covalent modifications of the ACSF molecule are included within the scope hereof. Such modifications are introduced into the encoded molecule by reacting targeted amino acid residues of the recovered protein with an organic derivatizing agent that is capable of combining with selected side chains or terminal residues, or by harnessing mechanisms of post-translational modification functioning in selected recombinant host cells. The resulting covalent derivatives are useful as immunogens or in programs directed at identifying residues important for biological activity. For example, complete inactivation of the biological activity of the protein after reaction with ninhydrin would suggest that at least one amino group is critical for its activity, whereafter the individual residues which were modified under the conditions selected are identified by isolation of a peptide fragment containing the modified amino acid residue.

Cysteinyl residues most commonly are reacted with α-haloacetates (and corresponding amines), such as iodoacetic acid or iodoacetamide to give carboxymethyl or carboxamidomethyl derivatives. Cysteinyl residues also are derivatized by reaction with bromotrifluoroacetone, α-bromo-β-(5-imidozoyl) propionic acid, chloroacetol phosphate, N-alkylmaleimides, 3-nitro-2-pyridyl disulfide, methyl 2-pyridyl disulfide, p-chloromercuribenzoate, 2-chloromercuri-4-nitrophenol or chloro-7-nitrobenzo-2-oxa-1,3-diazole. Since authentic ACSF is devoid of cysteine residues, organic derivatization would be applicable only to insertional or substitutional cysteine-containing ACSF variants, for example ACSF or its fragments in which an N or C-terminal cysteine has been inserted in order to facilitate cross-linking to an immunogenic peptide.

Histidyl residues preferably are derivatized by reaction with diethylpyrocarbonate at pH 5.5 to 7.0 because this agent is relatively specific for histidyl side chains. Parabromo-phenacyl bromide also is useful; the reaction should be performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α amino-containing residues include imidoesters such as methyl picolinimidate; pyridoxal phosphate; pyridoxal; borohydrides; trinitrobenzenesulfonic acid; O-methylisourea; 2,4-pentanedione; and transaminase-catalyzed reaction with glyoxylate.

Arginyl residues are modified by reaction with one of several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine ε-amino group.

The specific modification of tyrosyl residues per se has been extensively studied, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}$I or $^{131}$I to prepare labelled proteins for use in radioimmunoassay, the chloramine T method being widely adopted per se for this purpose.

Carboxyl side groups (aspartyl or glutamyl) are selectively modified by reaction with carbodiimides (R'—N=C=N—R') such as 1-cyclohexyl-3-(2-morpholinyl-(4)-ethyl) carbodiimide or 1-ethyl-3-(4-azonia-4,4-dimethylpentyl)-carbodiimide. Furthermore, aspartyl and glutamyl residues are converted to asparaginyl and glutaminyl residues by reaction with ammonium ions, this being an alternative to mutating the nucleic acid to encode asparagine are glutamine.

Derivatization with bifunctional agents is useful for preparing intermolecular aggregates, of the protein with immunogenic polypeptides as well as for cross-linking the protein to a water insoluble support matrix or surface for use in the assay or affinity purification of antibody. In addition, a study of intrachain cross-links will provide direct information on conformational structure. Commonly used cross-linking agents include 1,1-bis(diazoacetyl)-2-phenylethane, glutaraldehyde, N-hydroxysuccinimide esters, for example esters with 4-azidosalicylic acid, homobifunctional imidoesters including disuccinimidyl esters such as 3,3'-dithiobis (succinimidylpropionate), and bifunctional maleimides such as bis-N-maleimido-1,8-octane. Derivatizing agents such as methyl-3-[(p-azido-phenyl)dithio] propioimidate yield photactivatable intermediates which are capable of forming cross-links in the presence of light. Alternatively, reactive water insoluble matrices such as cyanogen bromide activated carbohydrates and the reactive substrates described in U.S. Pat. Nos. 3,969,287; 3,691,016; 4,195,128; 4,247,642; 4,229,537 and 4,330,440 are employed for protein immobilization.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues falls within the scope herein.

Other post-translational modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco pp 79–86 [1983]), acetylation of the N-terminal amine and, in some instances, amidation of the C-terminal carboxyl.

ACSF preferably is made by synthesis in recombinant cell culture. In order to do so, it is first necessary to secure nucleic acid that encodes ACSF. The sequence of the human cDNA encoding ACSF that was ultimately determined is shown in FIG. 2. Once this DNA has been identified it is a straight-forward matter for those skilled in the art to obtain it by nucleic acid hybridization to genomic libraries of human DNA or, if it is desired to obtain DNA encoding the ACSF of another animal species, then by hybridization of DNA libraries from cells of that species using radiophosphorylated λBRF52 cDNA. The hybridization analysis is now straight-forward because FIG. 2 enables the preparation of very long synthetic probes that are perfect or highly homologous complements to the target DNA.

It is possible that the cDNA or genomic library selected as the source for the ACSF nucleic acid will contain only partial clones for ACSF. These partial clones and fragments are readily assembled into full length ACSF DNA by cleaving the partial clones at selected restriction sites in overlapping sections, recovering each of the desired fragments and ligating them in the proper order and orientation. If necessary, oligonucleotides are prepared to supply any missing sequences.

The ACSF-encoding nucleic acid is then ligated into a replicable vector for further cloning or for expression. Vectors are useful for performing two functions in collaboration with compatible host cells (a host-vector system). One function is to facilitate the cloning of the nucleic acid that encodes the ACSF, i.e., to produce usable quantities of the nucleic acid. The other function is to direct the expression of ACSF. One or both of these functions are performed by the vector-host system. The vectors will contain different components depending upon the function they are to perform as well as the host cell that is selected for cloning or expression.

Each vector will contain nucleic acid that encodes ACSF as described above. Typically, this will be DNA that encodes mature ACSF linked at its amino terminus to a secretion signal. This secretion signal preferably is the ACSF presequence that normally directs the secretion of ACSF from human cells in vivo. However, suitable secretion signals also include signals from animal ACSF, the PTH signal, viral signals or signals from other secreted polypeptides of the same or related species.

Expression and cloning vectors contain a nucleic acid sequence that enables the vector to replicate in one or more selected host cells. Generally, in cloning vectors this sequence is one that enables the vector to replicate independently of the host chromosomes, and includes origins of replication or autonomously replicating sequences. Such sequences are well-known for a variety of bacteria, yeast and viruses. The origin of replication from the well-known plasmid pBR322 is suitable for most gram negative bacteria, the 2μ plasmid origin for yeast and various viral origins (SV40, polyoma, adenovirus, VSV or BPV) are useful for cloning vectors in mammalian cells. Origins are not needed for mammalian expression vectors. Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the expression host cell chromosome.

DNA also is cloned by insertion into the host genome. This is readily accomplished with bacillus species, for example, by including in the vector a DNA sequence that is complementary to a sequence found in bacillus genomic DNA. Transfection of bacillus with this vector results in homologous recombination with the genome and insertion of ACSF DNA. However, the recovery of genomic DNA encoding ACSF is more complex than that of an exogenously replicated vector because restriction enzyme digestion is required to excise the DNA.

Expression and cloning vectors should contain a selection gene, also termed a selectable marker. This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complement auxotrophic deficiencies, or (c) supply critical nutrients not available from complex media, e.g. the gene encoding D-alanine racemase for bacilli.

A suitable selection gene for use in yeast is the trp1 gene present in the yeast plasmid YRp7 (Stinchcomb et al., 1979, "Nature", 282: 39; Kingsman et al., 1979, "Gene", 7: 141; or Tschemper et al., 1980, "Gene", 10: 157). The trp1 gene provides a selection marker for a mutant strain of yeast lacking the ability to grow in tryptophan, for example ATCC No. 44076 or PEP4-1 (Jones, 1977, "Genetics", 85: 12). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

Examples of suitable selectable markers for mammalian cells are dihydrofolate reductase (DHFR), thymidine kinase and genes encoding resistance to hygromycin or neomycin. Such markers enable the identification of cells which were competent to take up the ACSF nucleic acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes ACSF. Amplification is the process by which genes in greater demand for the production of a protein critical for growth are reiterated in tandem within the chromosomes of successive generations of recombinant cells. Increased quantities of ACSF are synthesized from the amplified DNA.

For example, cells transformed with the DHFR selection gene are first identified by culturing all of the transformants in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, 1980, "Proc. Nat'l. Acad. Sci. USA" 77: 4216. A particularly useful DHFR is a mutant DHFR that is highly resistant to MTX (EP 117,060A). This selection agent can be used with any otherwise suitable host, e.g. ATCC No. CCL61 CHO-K1), notwithstanding the presence of endogenous DHFR. The DHFR and ACSF-encoding DNA then is amplified by exposure to an agent (methotrexate, or MTX) that inactivates the DHFR. One ensures that the cell requires more DHFR (and consequently amplifies all exogenous DNA) by selecting only for cells that can grow in successive rounds of ever-greater MTX concentration. Within the scope of this invention is initial selection of neo gene transformants with neomycin, followed by amplification of the DHFR amplifiable marker gene.

Other methods, vectors and host cells suitable for adaptation to the synthesis of the hybrid receptor in recombinant vertebrate cell culture are described in M. J. Gething et al., "Nature" 293: 620–625 (1981); N. Mantei et al., "Nature" 281: 40–46; and A. Levinson et al., EP 117,060A and 117,058A. Particularly useful starting plasmids for mammalian cell culture expression of ACSF are pE342.HBV E400.D22 (EP 117,058A), and pCIS2.8c24D (copending U.S. Ser. No. 907,297), expressly incorporated by reference.

Expression vectors, unlike cloning vectors, should contain a promoter which is recognized by the host organism and is operably linked to the ACSF nucleic acid. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. Any bacterial proteolytic degradation of ACSF which contains the native basic peptide domain would be reduced by the use of an inducible promoter to control transcription of the ACSF gene. At this time a large number of promoters recognized by a variety of potential host cells are well known. These promoters are operably linked to ACSF-encoding DNA by removing them from their gene of origin by restriction enzyme digestion, followed by insertion 5' to the start codon for ACSF. This is not to say that the genomic ACSF promoter is not usable for use in mammalian recombinant cell culture. However, heterologous promoters generally will result in greater transcription and higher yields of expressed ACSF.

Nucleic acid is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading phase. Linking is accomplished by ligation at convenient restriction sites. If such sites do not exist then synthetic oligonucleotide adaptors or linkers are used in accord with conventional practice.

Promoters suitable for use with prokaryotic hosts include the β-lactamase and lactose promoter systems (Chang et al., 1978, "Nature", 275: 615; and Goeddel et al., 1979, "Nature", 281: 544), alkaline phosphatase, a tryptophan (trp) promoter system (Goeddel 1980, "Nucleic Acids Res." 8: 4057 and EPO Appln. Publ. No. 36,776) and hybrid promoters such as the tac promoter (H. de Boer et al., 1983, "Proc. Nat'l. Acad. Sci. USA" 80: 21–25). However, other known bacterial promoters are suitable. Their nucleotide sequences have been published, thereby enabling a skilled worker operably to ligate them to DNA encoding ACSF (Siebenlist et al., 1980, "Cell" 20: 269) using linkers or adaptors to supply any required restriction sites. Promoters for use in bacterial systems also will contain a, Shine-Dalgarno (S.D.) sequence operably linked to the DNA encoding ACSF.

Suitable promoting sequences for use with yeast hosts include the promoters for 3-phosphoglycerate kinase (Hitzeman et al., 1980, "J. Biol. Chem.", 255: 2073) or other glycolytic enzymes (Hess et al., 1968, "J. Adv. Enzyme Reg.", 7: 149; and Holland, 1978, "Biochemistry", 17: 4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., EP 73,657A. Yeast enhancers also are advantageously used with yeast promoters.

ACSF transcription from vectors in mammalian host cells is controlled by promoters obtained from the genomes of viruses such as polyoma, cytomegalovirus, adenovirus, retroviruses, hepatitis-B virus and most preferably Simian Virus 40 (SV40), or from heterologous mammalian promoters, e.g. the actin promoter. The early and late promoters of the SV40 virus are conveniently obtained as an SV40 restriction fragment which also contains the SV40 viral origin of replication (Fiers et al, 1978, "Nature", 273: 113). Of course, promoters from the host cell or related species also are useful herein.

Transcription of ACSF-encoding DNA by higher eukaryotes is increased by inserting an enhancer sequence into the vector. An enhancer is a nucleotide sequence, usually about from 10–300 bp, that acts on a promoter to increase its transcription and does so in a manner that is relatively independent of its orientation and position. Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenoviral enhancers. The enhancer may be spliced into the vector at a position 5' or 3' to the ACSF-encoding sequence, but is preferably located at a site 5' from the promoter.

Expression vectors used in eukaryotic host cells (yeast, fungi, insect, plant, animal, human or nucleated cells from other multicellular organisms) also will contain sequences necessary for the termination of transcription and for stabilizing the mRNA. Such sequences are commonly available from the 5' and, occasionally 3' untranslated regions of eukaryotic or viral DNAs or CDNAs. These regions contain regions that are transcribed as polyadenylated segments in the untranslated portion of the mRNA encoding ACSF. The 3' untranslated regions also include transcription termination sites.

Suitable host cells for cloning or expressing the vectors herein are prokaryotes, yeast or higher eukaryotic cells. Prokaryotes include gram negative or gram positive organisms, for example *E. coli* or bacilli. A preferred cloning host is *E. coli* 294 (ATCC 31,446) although other gram negative or gram positive prokaryotes such as *E. coli* B, *E. coli* X1776 (ATCC 31,537), *E. coli* W3110 (ATCC 27,325), pseudomonas species, or *Serratia Marcesans* are suitable.

In addition to prokaryotes, eukaryotic microbes such as filamentous fungi or yeast are suitable hosts for ACSF-encoding vectors. *Saccharomyces cerevisiae*, or common baker's yeast, is the most commonly used among lower eukaryotic host microorganisms. However, a number of other genera, species and strains are commonly available and useful herein.

The preferred host cells for the expression of ACSF are cells derived from multicellular organisms. In principle, any eukaryotic cell from a multicellular organism is workable, whether from vertebrate or invertebrate culture, although cells from mammals are preferred. Propagation of such cells in culture is per se well known. See *Tissue Culture*, Academic Press, Kruse and Patterson, editors (1973). Examples of useful mammalian host cell lines are VERO and HeLa cells, Chinese hamster ovary cell lines, the WI38, BHK, COS-7, MDCK cell lines and human embryonic kidney cell line 293.

Host cells are transformed with the above-described expression or cloning vectors and cultured in conventional nutrient media modified as is appropriate for inducing promoters or selecting transformants containing amplified genes. The culture conditions, such as temperature, pH and the like, suitably are those previously used with the host cell selected for cloning or expression, as the case may be, and will be apparent to the ordinary artisan.

ACSF preferably is recovered from the culture medium as a secreted protein, although it also may be recovered from host cell lysates when directly expressed without a secretory signal. As a first step, the culture medium or lysate is centrifuged to remove particulate cell debris. Full length ACSF is purified from contaminant soluble proteins for example by adsorption on a cation exchange resin elution using a basic buffer, adsorption on an anti-ACSF immunoaffinity column and elution therefrom using pH 5–6 buffer. Alternatively, other processes such as chromatography on anion exchange and lectin affinity columns to remove contaminants are used for initial purification of ACSF-containing media or cell extracts. ACSF variants in which the basic peptide domain is deleted are best recovered by immunoaffinity or hydrophobic affinity chromatography.

Since native ACSF has a tendency to aggregate under some conditions it may be useful to stabilize the aggregative state of the multimers by providing in the separations a minor amount of a nonionic surfactant such as Tween or polyethylene glycol. A protease inhibitor such as PMSF also may be useful to inhibit proteolytic degradation during purification, and antibiotics may be included to prevent the growth of adventitious contaminants.

One skilled in the art will appreciate that purification methods suitable for native ACSF may require modification to account for changes in the character of ACSF or its variants upon expression in recombinant cell culture. Appropriate purification methods will be apparent to the artisan, depending upon the characteristics of the particular recombinant ACSF.

ACSF is prepared as a nontoxic salt with such ions as sodium, potassium, phosphate, chloride and the like. Generally, ACSF is stored in phosphate buffered saline or may be lyophilized in the presence of an excipient including sugar alcohols, e.g. mannitol or sorbitol; monosaccharides, e.g., glucose, manuose, galactose or fructose; oligosaccharides such as maltose, lactose or sucrose; and proteins such as human serum albumin.

The foregoing excipients also may contribute to the stability of ACSF to inactivation or precipitation upon aqueous storage, and may be used together with other stabilizers which are conventional per se. Such stabilizers include chelating agents, e.g. EDTA; acidic amino acids; and nonionic surfactants such as polyethylene glycol or block copolymers of polyethylene and polypropylene glycol.

ACSF antagonists, neutralizing antibodies for ACSF, or immunogens capable of raising neutralizing antibodies are administered to humans or animals in order to ameliorate HHM, and may have utility for the treatment of disorders characterized by hyperproliferation of keratinocytes, e.g. psoriasis. Therapeutic ACSF compositions will contain a therapeutically effective dose of ACSF antibody, antagonist or immunogen in a pharmacologically acceptable carrier. The dose, carrier and route of administration selected will depend, among other factors, upon the selection of antagonist or immunogen, the condition of the patient, the target disorder, the desired route of administration, and the activity of the selected ACSF variant. This is readily determined and monitored by the physician during the course of therapy.

The carrier for infusion or injection of ACSF is a sterile isotonic aqueous solution, for example saline for injection or 5% dextrose. These preparations are injected or infused by intranasal, subcutaneous, intravenous, intraperitoneal or other conventional routes of administration.

ACSF also is provided in a sustained release carrier. Suitable examples include semipermeable polymer matrices in the form of shaped articles, e.g. suppositories, or microcapsules. Implantable sustained release matrices include copolymers of L-glutamic acid and gamma ethyl-L-glutamate (U. Sidman et al., 1983, "Biopolymers" 22(1): 547–556), poly (2-hydroxyethyl-methacrylate) (R. Langer et al., 1981, "J. Biomed. Mater. Res." 15: 167–277 and R. Langer, 1982, "Chem. Tech." 12: 98–105), ethylene vinyl acetate (R. Langer et al., Id.), or poly-D-(−)-3-Hydroxybutyric acid (EP 133,988A). Sustained release ACSF compositions also include liposomally entrapped ACSF. Liposomes containing ACSF are prepared by methods known per se: DE 3,218,121A; Epstein et al., 1985, "Proc. Natl. Acad. Sci. USA" 82: 3688–3692; Hwang et al., 1980, "Proc. Natl. Acad. Sci. USA" 77: 4030–4034; EP 52322A; EP 36676A; EP 88046A; EP 143949A; EP 142641A; Japanese patent application 83-118008; U.S. Pat. Nos. 4,485,045 and 4,544,545; and EP 102,324A. Ordinarily the liposomes are of the small (about 200–800 Angstroms) unilamelar type in which the lipid content is greater than about 30 mol. % cholesterol, the selected proportion being adjusted for the optimal rate of ACSF leakage.

Polyclonal rabbit or murine antisera raised against ACSF are employed for immunoaffinity purification or ACSF in ELISA assays for ACSF and, when labelled with radiotechnetium or other comparable agents, for imaging of ACSF secreting tumors. Such antibodies also are labelled with cytotoxin for tumor cell targetting. Antibody specific for the unique C-terminus of ACSF is made by immunizing an animal against an immunogenic ACSF conjugate, e.g. an immunogenic fusion made in recombinant cell culture as described elsewhere herein, and thereafter screening for the presence of anti-C-terminal peptide titer by passing the antiserum through a column of immobilized ACSF (1-84) in order to adsorb antibodies directed against other ACSF epitopes, incubating the residual antibodies with $^{125}$I-ACSF to permit the C-terminal epitopes to bind to the anti-ACSF antibodies in the unadsorbed antibodies, and determining the amount of binding of $^{125}$I-ACSF, e.g. by adsorption on protein-A Sepharose. Alternatively, animals are immunized against the C-terminal peptide and antisera recovered. In either case, monoclonal antibodies are produced from the B cells of animals demonstrating titer against the C-terminal peptide. The availability of C-terminal specific antibody permits one to construct a sandwich immunoassay or competitive-type immunoassay in which PTH does not interfere. The sandwich assay is a method which comprises providing a first antibody capable of binding only to an epitope located between residues 1–84 of ACSF and a second antibody capable of binding only to an epitope located between residues 85–141 of ACSF, immobilizing either one of the first or second antibodies, contacting the immobilized antibody with the test sample in order to adsorb ACSF thereto, washing the bound ACSF, contacting the bound ACSF with the remaining one of said first or second antibodies, which remaining antibody has been labelled with a detectable group, in order to label the bound ACSF, and thereafter determining the amount of bound or free label.

In order to simplify the Examples certain frequently occurring methods will be referenced by shorthand phrases.

"Plasmids" are designated by a low case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors and other requirements as established by the enzyme suppliers were used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 2 units of enzyme in about 20 µl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, *Molecular Cloning* pp. 133–134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, "Nucleic Acids Res." 9:6103–6114, and D. Goeddel et al., 1980, "Nucleic Acids Res.: 8:4057.

"Transformation" or "transfection" means introducing DNA into an organism so that the DNA is replicable, either as an extrachromosomal element or chromosomal integrant. Unless otherwise provided, the method used herein for transformation of *E. coli* is the $CaCl_2$ method of Mandel et al., 1970, "J. Mol. Biol." 53: 154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

All literature citations herein are expressly incorporated by reference.

EXAMPLE 1

Clones of ACSF were isolated from a cDNA library of BEN cell mRNA probed with oligonucleotides synthesized based on N-terminal protein sequence data. Messenger RNA was purified from BEN cells by LiCl precipitation and oligo-dT cellulose chromatography. From this RNA, a library of oligo dT primed cDNA clones was generated in a λgt10 vector. From 2 µg of poly A+RNA 300 ng of double strand cDNA was synthesized. From about 1 ng of this cDNA over 1,000,000 clones were obtained. A portion of these clones were screened with a mixture of two 72-mer oligonucleotide probes, brf.1 and brf.2 (FIG. 1). The codon choice for these probes were based either on mammalian codon frequency tables (brf.1) or on the codons used for PTH at the homologous amino acids (brf.2). The oligonucleotides were end-labelled with $^{32}P$, hybridized to the library of cDNA clones in 20% formamide, 5× SSC at 42° C., and washed in 1× SSC at 42° C. From 250,000 clones screened, 6 positive clones were identified. The DNA sequence determined for these three clones is shown in FIG. 2.

In the course of examining positive clones hybridizing with the brf.2 probe a partial clone, λ57, was discovered which encodes a polypeptide remarkably homologous to the N-terminus of ACSF, but which is unlike ACSF C-terminal to the homologous region. Furthermore, the distance from the homologous region to the C-terminus of the λ57 polypeptide is only one residue shorter than PTH. Determination of the sequence for a complete clone which demonstrates further homology with ACSF would suggest that ACSF, PTH and this additional polypeptide are all members of a family of PTH-receptor active hormones.

Figure 3:
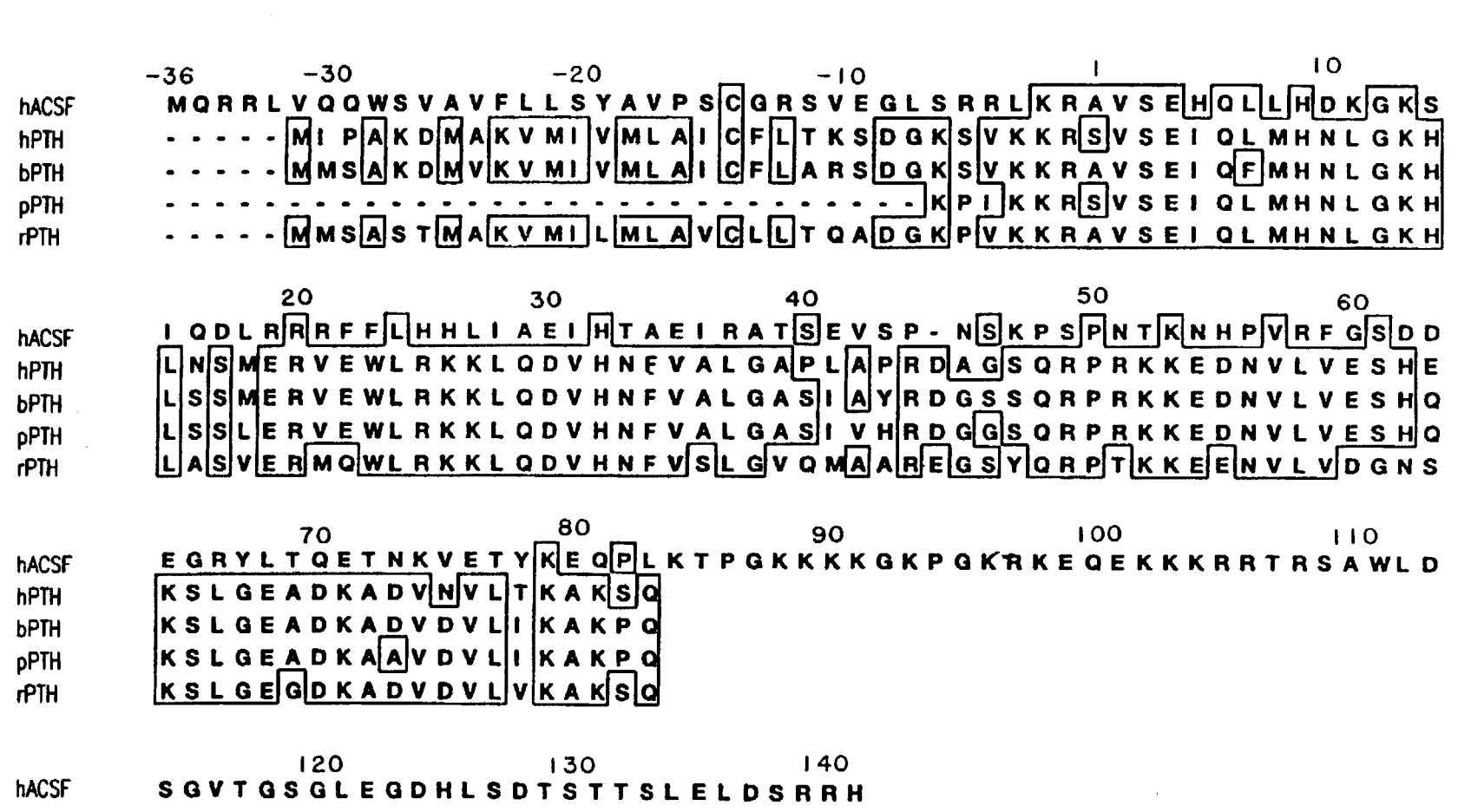

The DNA sequence for ACSF predicts a mature protein of 141 amino acids with a translated molecular weight of 16 kD. This is about the same as the molecular weight of 18–19 kD estimated for the purified BEN cell protein by SDS gel electrophoresis. The predicted sequence contains an excess of basic residues (29 K+R vs 20 D+E) accounting for the basic pI for this ACSF. The sequence predicts no potential N-linked glycosylation sites (NXS/T) and no cysteines in the mature protein. The sequence of ACSF shows some limited homology with PTH, most of it confined to the N-terminal 15 amino acids (FIG. 3).

The sequence of ACSF from amino acid 88 through 108 contains many basic residues and may be a region of protein cleavage which releases two peptides from one precursor. In this case the peptide from 1–87 would be expected to have adenylate cyclase stimulating activity in the same fashion that PTH 1–34 is active. The second functionality containing residues 109–141 would be a newly identified hormone.

The predicted mature protein is preceded by a 36 amino acid sequence beginning with a methionine. While this sequence has only a little homology with the prepro sequence of PTH, it does have an analogous prepro structure. The predicted mature ACSF sequence is preceded by a 5 amino acid pro sequence which has a number of basic residues like the 6 amino acid pro sequence of PTH. This putative pro sequence is preceded by a 31 amino acid sequence with a core of hydrophobic amino acids flanked by charged residues as expected for a signal sequence for secretion from the cell. The DNA sequence surrounding the proposed initiating ATG fits the consensus sequence found for the initiation of protein translation.

EXAMPLE 2

Figure 5:
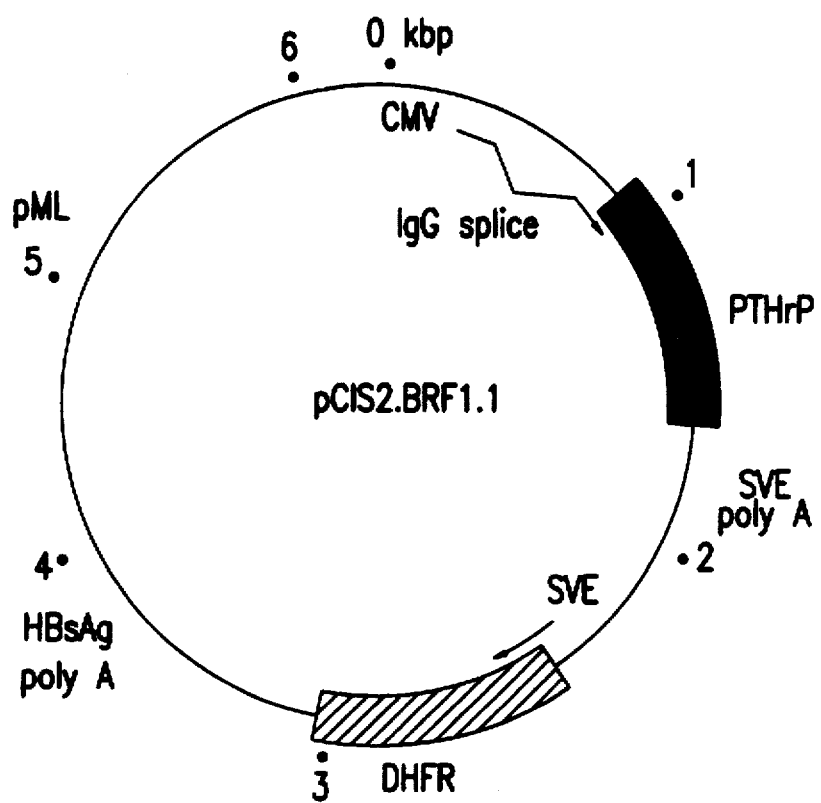
FIG. 5 shows the structure of the expression vector pCIS2.BRF1.1.

The cloned ACSF is spliced into a mammalian expression vector for secretion of the active protein from mammalian cells. FIG. 4 shows the steps undertaken to construct this expression vector, pCIS2.BRF1.1. The vector contains a cytomegalovirus promoter, immunoglobulin splice site, and an SV40 early polyadenylation signal as well as a DHFR transcription unit for stable expression and amplification in mammalian cells. This construct was performed by subcloning the 1341 bp insert from the primary cDNA clone, λBRF.52, into pUC119 to generate pBRF.52. Once the DNA sequence of this subclone was determined and the full length ACSF identified, the majority of the coding region was isolated on 932 bp HgaI to DraI fragment. Separately the mammalian expression vector, pCIS2.8c24D was cleaved with ClaI and HpaI and the 5340 bp fragment isolated. These two fragments and the double stranded oligonucleotide shown in FIG. 4 were ligated (after addition of a phosphate to the 5' end of the oligonucleotide) together to generate pCIS2.BRF1.1 (FIG. 5). The DNA sequence of the oligonucleotide insert was confirmed by sequencing.

The ACSF expression plasmid, pCIS2.BRF1.1, is transfected into mammalian cells by the calcium phosphate method for the expression of ACSF. COS-7 monkey kidney cells or 293 human kidney cells are suitable for transient expression; 293 human kidney cells or CHO (DBFR⁻) Chinese hamster ovary cells are suitable for stable expression using NEO cotransformation and G418 selection (293 cells) or by nutritional selection (CHO cells). ACSF is secreted from these cells and the pro sequence removed to generate active ACSF. The activity of the expressed ACSF is determined by assay of the culture supernatants for stimulation of cAMP levels in the osteoblast-like cell line, UMR-106. The expressed material is purified by an HPLC procedure similar to that used for the natural material secreted from BEN cells.

We claim:

1. An antibody which binds to an epitope located between residues 85–141 of Adenylate Cyclase Stimulation Factor (ACSF).

2. A composition comprising the antibody of claim 1 and a non-toxic excipient.

3. The composition of claim 1 which is free of antibody which binds to an epitome located between residues 1–84 of ACSF.

4. The composition of claim 2 which is free of antibody which binds to an epitope located between residues 109–141 of ACSF.

5. The antibody of claim 2 which is labelled with a detectable group.

6. A method for determining ACSF in a test sample comprising providing a first antibody which binds to an epitope located between residues 1–84 of ACSF and a second antibody which is the antibody of claim 1, immobilizing either one of the first or second antibodies, contacting the immobilized antibody with the test sample in order to adsorb ACSF thereto, washing the bound ACSF, contacting the bound ACSF with the remaining one of said first or second antibodies, which remaining antibody has been labelled with a detectable group, in order to label the bound ACSF, and thereafter determining the amount of bound or free label.

7. The antibody of claim 1 which is a monoclonal antibody.

8. The antibody of claim 1 which binds to a domain of ACSF consisting of residues 85–108 of ACSF.

9. The antibody of claim 1 which binds to a domain of ACSF consisting of residues 109–141 of ACSF.

10. The antibody of claim 1 which is immobilized by a water insoluble support.

11. A method of determining the presence of ACSF comprising contacting a test sample with the antibody of claim 1 and measuring the extent of antibody binding to the test sample.

12. The method of claim 10 wherein the antibody is labelled with a detectable group.

* * * * *